US009623414B2

(12) United States Patent
Ceremony et al.

(10) Patent No.: US 9,623,414 B2
(45) **Date of Patent: *Apr. 18, 2017**

(54) LOCALIZED TEMPERATURE CONTROL FOR SPATIAL ARRAYS OF REACTION MEDIA

(71) Applicant: Bio-Rad Laboratories, Inc., Hercules, CA (US)

(72) Inventors: Jeff Ceremony, Fairfield, CA (US); Daniel Y. Chu, San Francisco, CA (US)

(73) Assignee: Bio-Rad Laboratories, Inc., Hercules, CA (US)

( * ) Notice: Subject to any disclaimer, the term of this patent is extended or adjusted under 35 U.S.C. 154(b) by 307 days.

This patent is subject to a terminal disclaimer.

(21) Appl. No.: 14/567,121

(22) Filed: Dec. 11, 2014

(65) Prior Publication Data

US 2015/0258547 A1 Sep. 17, 2015

Related U.S. Application Data

(63) Continuation of application No. 12/652,611, filed on Jan. 5, 2010, now Pat. No. 8,945,881, which is a continuation of application No. 10/851,682, filed on May 20, 2004, now Pat. No. 7,771,933.

(60) Provisional application No. 60/472,964, filed on May 23, 2003.

(51) Int. Cl.

| | |
|---|---|
| ***C12Q 1/68*** | (2006.01) |
| ***B01L 7/00*** | (2006.01) |
| ***B01L 9/06*** | (2006.01) |
| *B01L 3/00* | (2006.01) |

(52) U.S. Cl.

CPC *B01L 7/52* (2013.01); *B01L 9/06* (2013.01); *B01L 3/50851* (2013.01); *B01L 7/54* (2013.01); *B01L 2300/044* (2013.01); *B01L 2300/0829* (2013.01); *B01L 2300/12* (2013.01); *B01L 2300/1805* (2013.01); *B01L 2300/1822* (2013.01); *B01L 2300/1838* (2013.01); *B01L 2300/1883* (2013.01); *B01L 2400/049* (2013.01); *B01L 2400/0475* (2013.01); *B01L 2400/0487* (2013.01)

(58) Field of Classification Search

None

See application file for complete search history.

(56) References Cited

U.S. PATENT DOCUMENTS

| | | | |
|---|---|---|---|
| 4,142,576 | A | 3/1979 | Perry et al. |
| 4,341,000 | A | 7/1982 | Stockman |
| 4,481,967 | A | 11/1984 | Frick |
| 4,516,631 | A | 5/1985 | Russell |
| 4,703,796 | A | 11/1987 | Meijer et al. |
| 4,851,183 | A | 7/1989 | Hampel |
| 4,970,868 | A | 11/1990 | Grebe et al. |
| 5,498,392 | A | 3/1996 | Wilding et al. |
| 5,589,136 | A | 12/1996 | Northrup et al. |
| 5,598,320 | A | 1/1997 | Toedtman et al. |
| 5,639,423 | A | 6/1997 | Northrup et al. |
| 5,646,039 | A | 7/1997 | Northrup et al. |
| 5,674,742 | A | 10/1997 | Northrup et al. |
| 5,720,923 | A | 2/1998 | Haff et al. |
| 5,817,167 | A | 10/1998 | DesChamps |
| 5,849,208 | A | 12/1998 | Hayes et al. |
| 5,921,315 | A | 7/1999 | Dinh |
| 5,928,907 | A | 7/1999 | Woudenberg et al. |
| 5,935,522 | A | 8/1999 | Swerdlow et al. |
| 5,946,191 | A | 8/1999 | Oyamada |
| 5,947,111 | A | 9/1999 | Neulander et al. |
| 6,124,138 | A | 9/2000 | Woudenberg et al. |
| 6,126,899 | A | 10/2000 | Woudenberg et al. |
| 6,145,688 | A | 11/2000 | Smith |
| 6,174,670 | B1 | 1/2001 | Wittwer et al. |
| 6,225,061 | B1 | 5/2001 | Becker et al. |
| 6,232,079 | B1 | 5/2001 | Wittwer et al. |
| 6,245,514 | B1 | 6/2001 | Wittwer |
| 6,312,929 | B1 | 11/2001 | McMillan |
| 6,334,980 | B1 | 1/2002 | Hayes et al. |
| 6,337,435 | B1 | 1/2002 | Chu et al. |
| 6,369,893 | B1 | 4/2002 | Christel et al. |
| 6,372,484 | B1 | 4/2002 | Ronchi et al. |
| 6,413,766 | B2 | 7/2002 | Landers et al. |
| 6,432,695 | B1 | 8/2002 | Zou et al. |
| 6,503,750 | B1 | 1/2003 | Benett et al. |
| 6,509,186 | B1 | 1/2003 | Zou et al. |
| 6,521,181 | B1 | 2/2003 | Northrup et al. |
| 6,521,447 | B2 | 2/2003 | Zou et al. |
| 6,524,532 | B1 | 2/2003 | Northrup |
| 6,633,785 | B1 | 10/2003 | Kasahara et al. |
| 6,640,891 | B1 | 11/2003 | Oldenburg |

(Continued)

FOREIGN PATENT DOCUMENTS

| | | | |
|---|---|---|---|
| AU | 774199 | B2 | 6/2004 |
| EP | 0 963 250 | | 12/1999 |

(Continued)

OTHER PUBLICATIONS

International Search Report from PCT/US2007/072261, dated Apr. 11, 2008 (2 pages).

(Continued)

*Primary Examiner* — Stephanie K Mummert

(74) *Attorney, Agent, or Firm* — Kilpatrick Townsend & Stockton LLP

(57) ABSTRACT

Individual temperature control in multiple reactions performed simultaneously in a spatial array such as a multi-well plate is achieved by thermoelectric modules with individual control, with each module supplying heat to or drawing heat from a single region within the array, the region containing either a single reaction vessel or a group of reaction vessels.

16 Claims, 12 Drawing Sheets

(56) References Cited

U.S. PATENT DOCUMENTS

| | | | |
|---|---|---|---|
| 6,706,519 B1 | 3/2004 | Kellogg et al. | |
| 6,710,442 B1 | 3/2004 | Lindgren et al. | |
| 6,717,365 B2 | 4/2004 | Lee et al. | |
| 6,767,512 B1 | 7/2004 | Lurz et al. | |
| 6,875,602 B2 | 4/2005 | Gutierrez | |
| 6,939,477 B2 | 9/2005 | Stark et al. | |
| 6,960,437 B2 | 11/2005 | Enzelberger et al. | |
| 7,074,367 B2 | 7/2006 | Lurz et al. | |
| 7,771,933 B2 | 8/2010 | Arciniegas et al. | |
| 8,945,881 B2 * | 2/2015 | Arciniegas ................ | B01L 7/52<br>435/289.1 |
| 2002/0006619 A1 | 1/2002 | Cohen et al. | |
| 2003/0008286 A1 | 1/2003 | Zou et al. | |
| 2004/0043479 A1 | 3/2004 | Briscoe et al. | |
| 2006/0246573 A1 | 11/2006 | Kurane et al. | |

FOREIGN PATENT DOCUMENTS

| | | | |
|---|---|---|---|
| JP | 55-0822091 | A | 6/1980 |
| JP | H03-297378 | A | 12/1991 |
| JP | H08-189788 | A | 7/1996 |
| WO | 98/43740 | A2 | 10/1988 |
| WO | 99/48608 | A2 | 9/1999 |
| WO | 01/07890 | A2 | 2/2001 |
| WO | 01/08800 | A2 | 2/2001 |
| WO | 01/51209 | A1 | 7/2001 |
| WO | 03/076661 | A1 | 9/2003 |

OTHER PUBLICATIONS

As-filed U.S. Appl. No. 13/487,414, filed Jun. 4, 2012.

Office Action from U.S. Appl. No. 13/487,414, dated Dec. 30, 2013.

* cited by examiner

LOCALIZED TEMPERATURE CONTROL FOR SPATIAL ARRAYS OF REACTION MEDIA

CROSS-REFERENCES TO RELATED APPLICATIONS

This application is a continuation of U.S. patent application Ser. No. 12/652,611, filed Jan. 5, 2010, which is a continuation of U.S. patent application Ser. No. 10/851,682, filed May 21, 2004 (now U.S. Pat. No. 7,771,933, issued Aug. 10, 2010), which claims benefit from U.S. Provisional Patent Application No. 60/472,964, filed May 23, 2003. The contents of all such applications are incorporated herein by reference in their entirety.

BACKGROUND OF THE INVENTION

1. Field of the Invention

This invention relates to sequential chemical reactions of which the polymerase chain reaction (PCR) is one example. In particular, this invention addresses the methods and apparatus for performing chemical reactions simultaneously in a multitude of reaction media and independently controlling the reaction in each medium.

2. Description of the Prior Art

PCR is one of many examples of chemical processes that require precise temperature control of reaction mixtures with rapid temperature changes between different stages of the procedure. PCR itself is a process for amplifying DNA, i.e., producing multiple copies of a DNA sequence from a single strand bearing the sequence. PCR is typically performed in instruments that provide reagent transfer, temperature control, and optical detection in a multitude of reaction vessels such as wells, tubes, or capillaries. The process includes a sequence of stages that are temperature-sensitive, different stages being performed at different temperatures and the temperature being cycled through repeated temperature changes.

While PCR can be performed in any reaction vessel, multi-well reaction plates are the reaction vessels of choice. In many applications, PCR is performed in "real-time" and the reaction mixtures are repeatedly analyzed throughout the process, using the detection of light from fluorescently-tagged species in the reaction medium as a means of analysis. In other applications, DNA is withdrawn from the medium for separate amplification and analysis. In multiple-sample PCR processes in which the process is performed concurrently in a number of samples, a preferred arrangement is one in which each sample occupies one well of a multi-well plate or plate-like structure, and all samples are simultaneously equilibrated to a common thermal environment at each stage of the process. In some cases, samples are exposed to two thermal environments to produce a temperature gradient across each sample.

In the typical PCR instrument, a 96-well plate with a sample in each well is placed in contact with a metal block that is heated and cooled either by a Peltier heating/cooling apparatus or by a closed-loop liquid heating/cooling system that circulates a heat transfer fluid through channels machined into the block. Certain instruments, such as the SMART CYCLER® II System sold by Cepheid (Sunnyvale, Calif., USA), provide different thermal environments in different reaction vessels by using individual reaction vessels or capillaries. These instruments are costly and unable to reliably achieve temperature uniformity. The Institute of Microelectronics, of Singapore, likewise offers an instrument that provides multiple thermal environments, but does so by use of an integrated circuit to create individual thermal domains. This method is miniaturized but does not allow the use of multi-well reaction plates, which are generally termed microplates.

SUMMARY OF THE INVENTION

The present invention provides means for independently controlling the temperature in discrete regions of a spatial array of reaction zones, thereby allowing different thermal domains to be created and maintained in a single multi-well plate rather than requiring the use of individual reaction vessels, capillaries, or devices fabricated in the manner of integrated circuit boards or chips. The invention thus allows two or more individualized PCR experiments to be run in a single plate. With this invention, PCR experiments can be optimized and comparative experiments can be performed. The wells of the plate can thus be grouped into subdivisions or regions, each region containing either a single well or a group of two or more wells, and different regions can be maintained at different temperatures while all wells in a particular region are maintained under the same thermal control. A multitude of procedures can then be performed simultaneously with improved uniformity and reliability within each zone, together with reductions in cost and complexity.

BRIEF DESCRIPTION OF THE DRAWINGS

All Figures accompanying this specification depict structures within the scope of the present invention.

DETAILED DESCRIPTION OF THE INVENTION AND PREFERRED EMBODIMENTS

Figure 1:
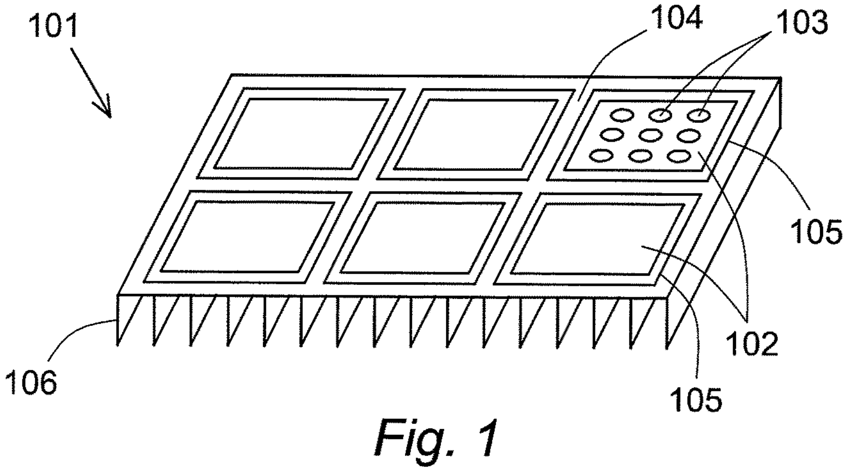
FIG. 1 is a perspective view of a PCR plate or other multi-well reaction plate with localized temperature control in portions of the plate.

This invention applies to spatial arrays of reaction zones in which the arrays are either a linear array, a two-dimensional array, or any fixed physical arrangement of multiple reaction zones. The receptacles in which these arrays are retained are typically referred to as sample blocks, the samples being the reaction mixtures in which the PCR process is performed. As of the date of filing of the application on which this patent will issue, the invention is of particular interest to sample blocks that form planar two-dimensional arrays of reaction zones, and most notably microplates of various sizes. The most common microplates are those with 96 wells arranged in a standardized planar rectangular array of eight rows of twelve wells each, with standardized well sizes and spacings. The invention is likewise applicable to plates with fewer wells as well as plates with greater numbers of wells.

Independent temperature control in each region of the sample block in accordance with this invention is achieved by a plurality of thermoelectric modules, each such module thermally coupled to one region of the block with a separate module for each region. In preferred embodiments of this invention, thermal barriers of any of various forms thermally insulate each region from adjacent regions, and each module is electrically connected to a power supply in a manner that permits independent control of the magnitude of the electric power delivered to each module and, in preferred embodiments, the polarity of the electric current through each module.

The thermoelectric modules, also known as Peltier devices, are units widely used as components in laboratory instrumentation and equipment, well known among those familiar with such equipment, and readily available from commercial suppliers of electrical components. Thermoelectric devices are small solid-state devices that function as heat pumps, operating under the theory that when electric current flow through two dissimilar conductors, the junction of the two conductors will either absorb or release heat depending on the direction of current flow. The typical thermoelectric module consists of two ceramic or metallic plates separated by a semiconductor material, of which a common example is bismuth telluride. In addition to the electric current, the direction of heat transport can further be determined by the nature of the charge carrier in the semiconductor (i.e., N-type vs. P-type). Thermoelectric modules can thus be arranged and/or electrically connected in the apparatus of the present invention to heat or to cool the region of reaction zones. A single thermoelectric module can be as thin as a few millimeters with surface dimensions of a few centimeters square, although both smaller and larger devices exist and can be used. Thermoelectric modules can be grouped together to control the temperature of a region of the sample block whose lateral dimensions exceed those of a single module. Alternatively the lateral dimensions of the module itself can be selected to match those of an individual region.

In embodiments of this invention in which adjacent regions of the sample block are thermally insulated from each other, such insulation can be achieved by air gaps or voids, or by embedding solid thermal barriers with low thermal conductivity in the sample block. Examples of thermally insulating solid materials are foamed plastics such as polystyrene, poly(vinyl chloride), polyurethanes, and polyisocyanurates.

Thermal coupling of the thermoelectric modules to the regions of the sample block is accomplished by any of various methods known in the art. Examples are thermally conductive adhesives, greases, putties, or pastes to provide full surface contact between the thermoelectric modules and the sample block.

Further examples, particularly ones that offer individual control, are heat pipes. Heat pipes of conventional construction that are commonly used for heat transfer and temperature control, particularly the types that are used in laptop and desktop computers, can be used. The typical heat pipe is a closed container, most commonly a tube, with two ends, one designated a heat receiving end and the other a heat dissipating end, and with a volatile working fluid retained in the container interior. The working fluid continuously transports heat from the heat receiving end to the heat dissipating end by an evaporation-condensation cycle. Depending on the orientation of the heat pipe and the direction in which heat is to be transported, the return of the condensed fluid from the heat dissipating end to the heat receiving end to complete the cycle can be achieved either by gravity or by a fluid conveying means such as a wick or capillary structure within the heat pipe to convey the flow against gravity.

The working fluid in a heat pipe will be selected on the basis of the heat transport characteristics of the fluid. Prominent among these characteristics are a high latent heat, a high thermal conductivity, low liquid and vapor viscosities, and high surface tension. Additional characteristics of value in many cases are thermal stability, wettability of wick and wall materials, and a moderate vapor pressure over the contemplated operating temperature range. With these considerations in mind, both organic and inorganic liquids can be used, the optimal choice depending on the contemplated temperature range. For PCR systems, a working fluid with a useful range of from about 50° C. to about 100° C. will be most appropriate. Examples are acetone, methanol, ethanol, water, toluene, and various surfactants.

In heat pipes in which a wick or capillary structure returns the working fluid to the heat receiving end, such structures are known in the art of heat pipes and assume various forms. Examples are porous structures, typically made of metal foams or felts of various pore sizes. Further examples are fibrous materials, notably ceramic fibers or carbon fibers. Wicks can be formed from sintered powders or screen mesh, and capillaries can assume the form of axial grooves in the heat pipe wall or actual capillaries within the heat pipe. The wick or capillary structure can be positioned at the wall of the heat pipe while the condensed working fluid flows through the center of the pipe. Alternatively, the wick or capillary structure can be positioned in the center or bulk region of the heat pipe while the condensed working fluid flows down the pipe walls.

In preferred embodiments of the invention in which heat pipes are used, devices or structures are incorporated into the heat pipe design to permit individual control of the rate at which the condensed fluid is returned or conveyed. This provides further individual heat control in addition to the individual heat control provided by the thermoelectric modules. This control over the return rate of the condensed fluid can be achieved by incorporating elements in the wick that respond to externally imposed influences, such as electric or magnetic fields, heat, pressure, and mechanical forces, as well as laser beams, ultrasonic vibrations, radiofrequency and other electromagnetic waves, and magnetostrictive effects. Control can likewise be achieved by using a working fluid that responds to the same types of influences. If the wick contains a magnetically responsive material, for example, movement of the wick or forces within the wick can be controlled by the imposition of a magnetic field. This is readily achieved and controlled by an external electromagnetic coil. Mechanical pressure within the wick can be applied and controlled by piezoelectric elements or by flow-regulating elements such as solenoid valves.

In various embodiments of this invention, heat sinks are included as a component of the apparatus to receive or dissipate the heat discharged by a thermoelectric device or a heat pipe, or both. Conventional heat sinks such as fins and circulating liquid or gaseous coolants can be used.

Still further types of thermal coupling between the thermoelectric devices and the sample block can be achieved by a variety of methods other than heat pipes that still allow variations from one region of the sample block to the next with individual control. Like the individual heat pipe control, these further methods of thermal coupling control can be achieved by the use of thermal coupling materials that are responsive to external influences, such as electromagnetic waves, magnetic or electric fields, heat, and mechanical pressure. Examples of such thermal coupling materials are suspensions or slurries of electrically responsive particles, magnetically responsive particles, piezoelectric elements, and compressive or elastic materials. Externally imposed influences that can vary the thermal coupling of these materials are localized electric, notably alternating current, fields, localized magnetic fields, and mechanical plungers exerting localized pressures.

The Figures hereto depict certain examples of ways in which the present invention can be implemented and are not intended to define or to limit the scope of the invention.

FIG. 1 illustrates a PCR plate 101 constructed from six sample blocks 102, each block containing an array of wells 103 and serving as a thermal domain separate from the remaining blocks. The six blocks in this example collectively constitute the spatial array of reaction zones, each block representing a separate "region" in the array, as these terms are used herein. Between each adjacent pair of sample blocks is an air gap 104 to thermally isolate the blocks from each other. An alternative to an air gap is an insert of low thermal conductivity material. Beneath each block is a Peltier device (thermoelectric module) 105. The modules operate independently but share a common heat sink 106. In addition to its heat removal function, the common heat sink serves as a support base for the entire assembly, providing mechanical integrity to the arrangement of the sample blocks and fixing the widths of the air gaps between the sample blocks. The sample blocks can be individually secured to the heat sink with a non-thermally-conducting device such as a plastic screw or other piece of hardware that has low thermal conductivity.

Figure 2:
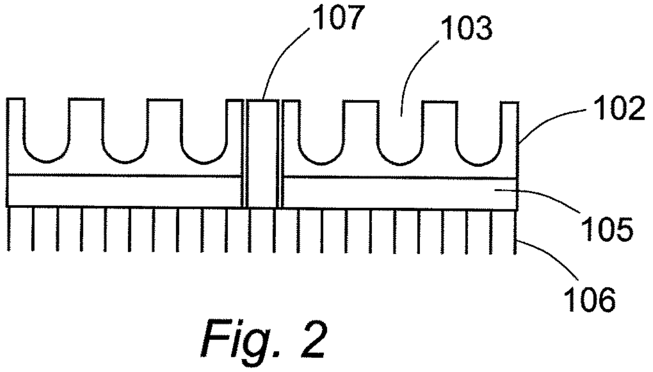
FIG. 2 is a cross section of a plate similar to that of FIG. 1 in which a thermal barrier is positioned between adjacent regions in the plate.

FIG. 2 is a side view of the structure of FIG. 1, showing the embodiment in which a solid barrier 107 of thermally insulating material such as low-conductivity plastic is inserted between adjacent blocks 102 and also between adjacent Peltier devices 105 while a common heat sink 106 provides structural integrity to all blocks.

An alternative to the use of individual sample blocks for each thermal domain is a single block in which individual thermal domains are delineated by slits defining the boundaries of each domain. Insulating shims or cast-in-place insulating barriers, formed of either plastic or any material of low thermal conductivity can be used in place of the slits or inserted in the slits. A separate Peltier device is used for each thermal domain with a common heat sink for all domains. The single block will be of thermally conducting material such as an aluminum plate.

Figure 3:
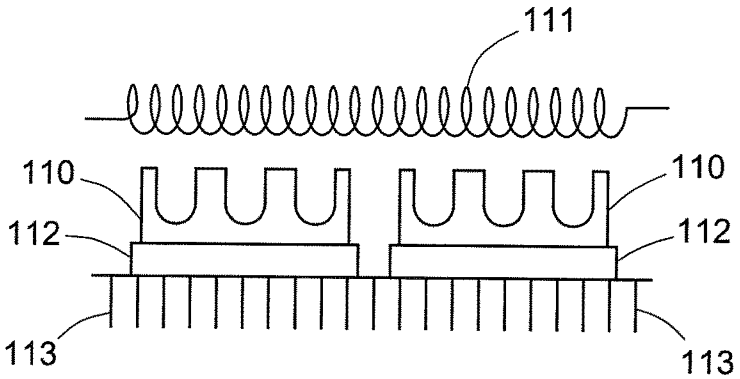
FIG. 3 is a cross section of a plate similar to those of the preceding figures, with an added heating element supplying heat to the entire plate.

A configuration that is the reverse of those of FIGS. 1 and 2 is shown in FIG. 3, in which Peltier devices are used for cooling rather than heating, in conjunction with a heater that supplies heat to all thermal domains. Individual sample blocks 110 define the individual thermal domains, and are held in a rigid planar configuration by structural elements that are not shown in the drawing. Alternatively, regions of a multi-well plate can replace the individual sample blocks. Positioned above the array of sample blocks is a single heating element 111 extending over the entire array, and thermally coupled to the bottom of each sample block is an individually controlled Peltier device 112. Separate temperatures for the various sample blocks are thus achieved by varying the cooling rates in the Peltier devices. The heating element 111 can be any element that supplies heat over a broad area. Examples are a resistance heater, an induction heater, a microwave heater, and an infrared heater. At the heat-discharging side of each Peltier device is a heat sink 113 as described above.

Figure 4:
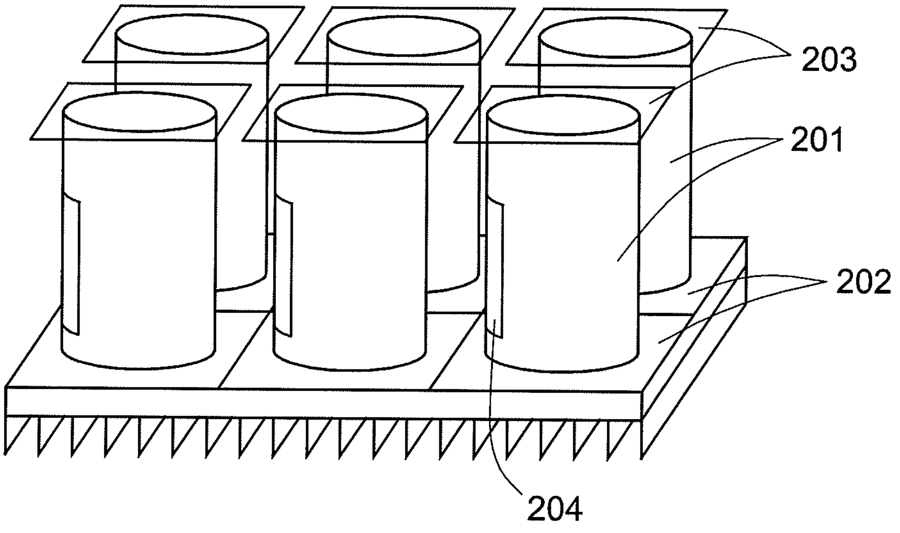
FIG. 4 is a perspective view of a temperature control system for PCR or other multi-well reaction plate, utilizing individual heat pipes for each thermal domain.

FIG. 4 illustrates a construction that utilizes heat pipes 201 for thermal coupling of the Peltier devices 202 to the individual thermal domains in the spatial array of reaction zones. Temperature control for each individual domain is provided by a combination of a separate Peltier device and a separate heat pipe. Each heat pipe is thermally coupled at its heat receiving end (i.e., its evaporating end) to a Peltier device and thermally coupled at its heat dissipating end (i.e., its condensing end) to an individual reaction well or group of reaction wells. Conversely, any single heat pipe can be oriented for heat transfer in the reverse direction, with its heat receiving end thermally coupled to the reaction well(s) and its heat dissipating end thermally coupled to the Peltier device. In this reverse configuration, the Peltier device serves as a cooling element, and a separate heating element such as a film heater 203 supplies heat to the reaction wells. Either a single film heater common to all wells or groups of wells is used or individual film heaters for each well or group.

Figure 5A:
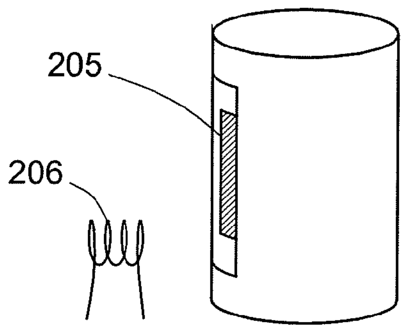
FIGS. 5*a* through 5*e* are perspective views of five different heat pipe configurations for use in the system of FIG. 4.
Figure 5B:
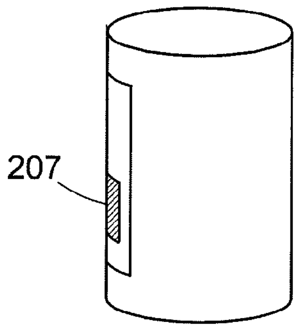
Figure 5C:
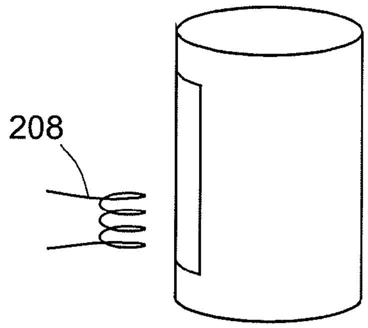
Figure 5D:
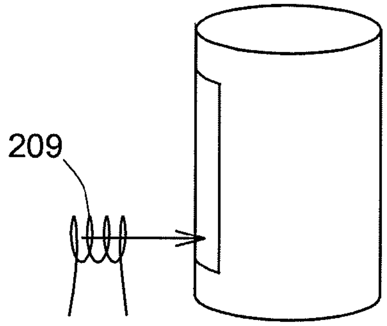
Figure 5E:
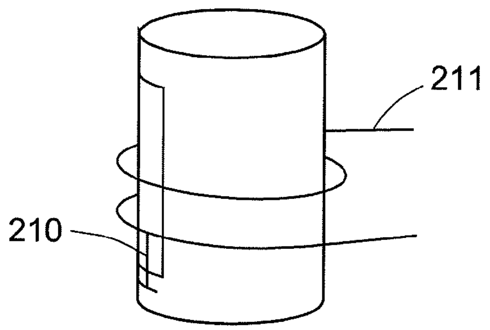

The temperature in any single thermal domain is controlled in part by the Peltier device and in part by the heat pipe. Each of the heat pipes shown has a wicking zone 204 on an area of the pipe wall, and the heat transfer rate through the pipe is controllable by modulating the wicking action in the wicking zone. Modulation can be achieved in any of several ways. FIG. 5*a*, for example, illustrates a heat pipe with a wicking zone that contains a magnetically responsive material 205. This material or the entire wicking zone can be caused to move by exerting a magnetic field on the heat pipe, which is readily done by an electromagnetic coil 206. The magnitude and polarity of the current passing through the coil can be varied, thereby modulating the rate of flow of the working fluid through the wicking zone. Another example is represented by FIG. 5*b* where piezoelectric elements 207 are embedded in the wall at the wicking zone. Electric field variations in the piezoelectric elements can cause pressure changes leading to the opening or closing of the wicking zone area. This again modulates the flow rate of working fluid. A third example is represented by FIG. 5*c*, in which the movement of fluid through the wicking zone is driven by, and controlled by, localized heating from an external heating element 208. A fourth example is represented by FIG. 5*d* in which an external solenoid valve 209 is used to either open and close flow passages in the wicking zone or to apply mechanical pressure to the wicking zone as a means to modulate the fluid flow. A fifth example is represented by FIG. 5*e* where the heat pipe contains an internal valve 210 that is controlled magnetically by an external electromagnetic coil 211, or by external pressure, to modulate the fluid flow.

Figure 6:
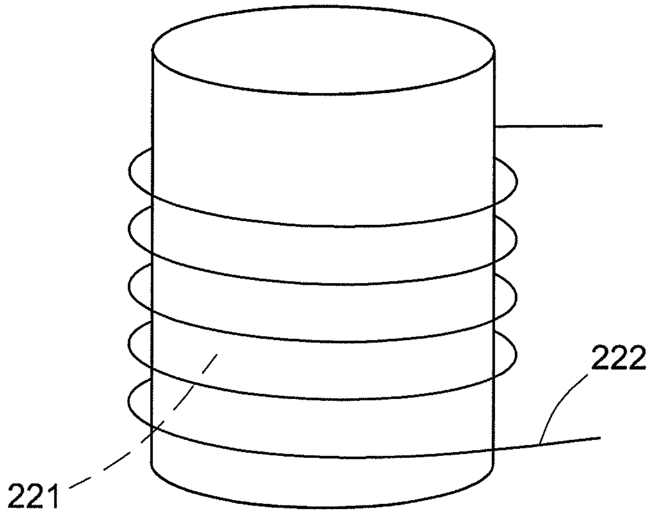
FIG. 6 is a perspective view of a sixth heat pipe configuration for use in the system of FIG. 4.

An alternative method of modulating the heat transfer rate through a heat pipe is by modulating the bulk movement of the working fluid. The structure depicted in FIG. 6 uses a magnetically responsive fluid 221 as the working fluid, and contains an electrical coil 222 wound around the pipe. The magnetic field created by the coil causes motion of the magnetically responsive fluid, either accelerating or decelerating the flow of the fluid through the evaporation-condensation cycle. A wicking zone can also be present and can operate in conjunction with the response of the working fluid to the magnetic field. Alternatively, the magnetically responsive working fluid and coil can serve as a substitute for the wicking zone. Common magnetically responsive fluids are suspensions of magnetic particles in a liquid suspending medium.

Figure 7:
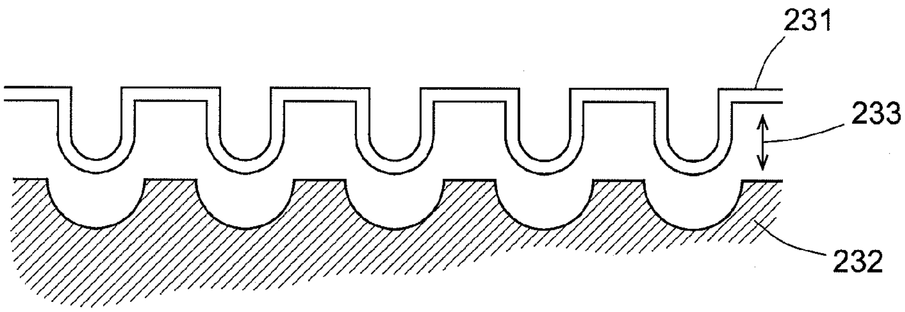
FIG. 7 is a cross section of a plate and heat transfer block for use in the systems of the preceding figures.

Further variation and control of the thermal domains in accordance with this invention can be achieved by adding variations in the thermal coupling between each region (i.e., each well or group of wells) in a multi-well plate and the heating or cooling units beneath the plate. In the illustrative structure shown in FIG. 7, the sample plate 231 is poised above a support block 232 of high heat conductivity, with a gap 233 of variable width between the plate and the block. The width of the gap can be changed by the use of mechanical motors, piezoelectrics, magnetic voice coils, or pneumatic pressure drives. While FIG. 7 shows a single thermal domain, an array of similar thermal domains will have independent means for varying the gap width.

Figure 8A:
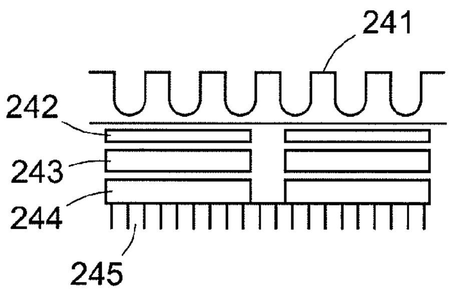
FIGS. 8*a* through 8*f* are cross sections of six different variable thermal coupling systems for use in the temperature control systems of the preceding figures.
Figure 8B:
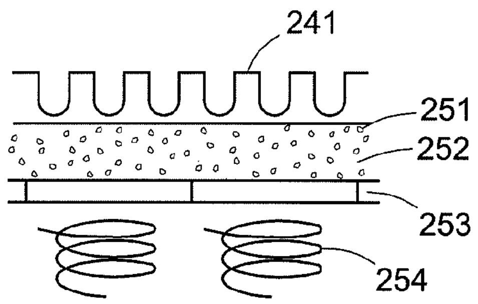

Variable thermal coupling can also be achieved by using thermal couplers of different types, as shown in FIGS. 8*a* through 8*f*. The sample block 241, which may be a multi-well plate or a support block on which the multi-well plate rests, appears at the top of each Figure. FIG. 8*a* shows a separate heater 242 for each thermal domain with variable thermal couplings 243, an array of Peltier devices 244, one for each thermal domain, and a common heat sink 245. FIG. 8*b* shows the use of non-magnetic but electrically conductive particles 251, such as aluminum, in a thermal paste or slurry 252, thermally coupling an array of Peltier devices 253 of non-magnetic material to the sample block, with an array of AC electrical coils 254 positioned below the Peltier devices 253. A current passed through any individual coil 254 causes eddy-current repulsion which produces localized electrical fields within the particle slurry. Localized electrical fields of different magnitude produce different degrees of repulsion of the particles in the slurry, and since particles will draw closer to each other as the repulsion between them decreases, the thermal conductivity of the slurry rises as the repulsion drops.

Figure 8C:
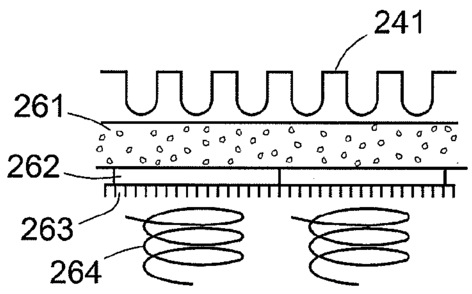

In FIG. 8*c*, a magnetic fluid or suspension of magnetic particles 261 whose thermal conductivity varies with variations in the local magnetic field is placed between the sample block 241 and the Peltier devices 262, with appropriate heat sinks 263 below the Peltier devices. Magnetic coils 264 positioned below the Peltier devices and heat sinks produce local magnetic fields in the magnetic fluid, and differences among the various coils in the magnitude of the current produce differences in the local magnetic fields within the magnetic fluid and thereby the proximity between the sample block and the Peltier device adjacent to the localized field.

Figure 8D:
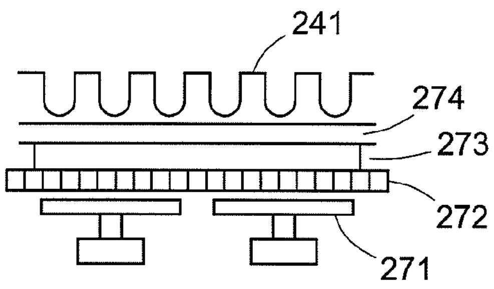
Figure 8E:
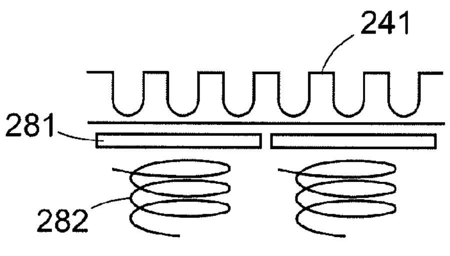

Thermal contact can also be varied by applying varying mechanical pressure to compress the heating or cooling block against the plate, with different pressure applied to achieve different degrees of thermal contact. FIG. 8*d* illustrates a structure that operates in this manner. Individually controlled mechanical plungers 271 apply pressure to the heat sink 272, Peltier devices 273, and a compressible thermal coupling 274. FIG. 8*e* shows an alternative arrangement in which the sample block 241 or heat sink 281 is made of magnetic material, and different pressures and therefore degrees of contact are achieved by applying different magnetic fields as a result of different electrical currents passed through individual coils 282 below the heat sink.

Figure 8F:
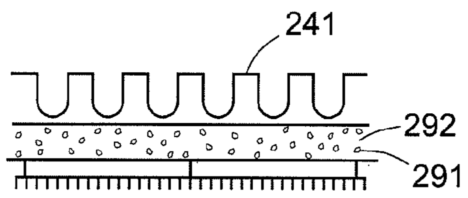

Similar effects can be achieved with piezoelectrics 291 suspended in a slurry of thermal grease 292, as illustrated in FIG. 8*f*. Voltage can be supplied to the piezoelectrics in a variety of ways. For example, wires can contact individual piezoelectric elements. A voltage is then applied through the wires by a microprocessor-controlled voltage source with the piezoelectric elements wired in parallel. The voltage can be as high as several hundred volts. Alternatively, the piezoelectric elements can be powered by radiofrequency (RF) waves. To accomplish this, each piezoelectric element will have transponder circuitry that detects and converts RF fields to voltage. The amplitude of the DC source can be increased by a microchip DC-DC converter to the voltage necessary to significantly flex the piezoelectrics. Since currents of very small magnitude (on the order of microamps) are sufficient, the detected RF energy conversion can be used without wire connections to the piezoelectrics. A further alternative is the use of capacitative coupling to individual circuitry on the piezoelectrics, utilizing RF or sub-RF fields. The induced electric charge and the DC-DC conversion will control and/or flex the piezoelectrics. A still further alternative is to use inductive coupling to circuitry on the individual piezoelectrics, again using RF or sub-RF fields. The induced electric current will charge a capacitor, and DC-DC conversion is then used to control and/or flex the piezoelectrics. Varying the voltage on the piezoelectrics 291 by any of these methods produces localized variations in pressure in the slurry 292 and thereby variations in the thermal coupling. The piezoelectrics 291 undergo minute movement in the slurry, thereby modulating the thermal coupling.

Temperature control in each of the thermal domains as well as the individual reaction media can be increased by the use of specialized sample plates that are designed to allow faster thermal equilibration between the contents of a sample well and the temperature control element, particularly when the element is a Peltier device or any of the various types of thermal couplings described above.

Figure 9:
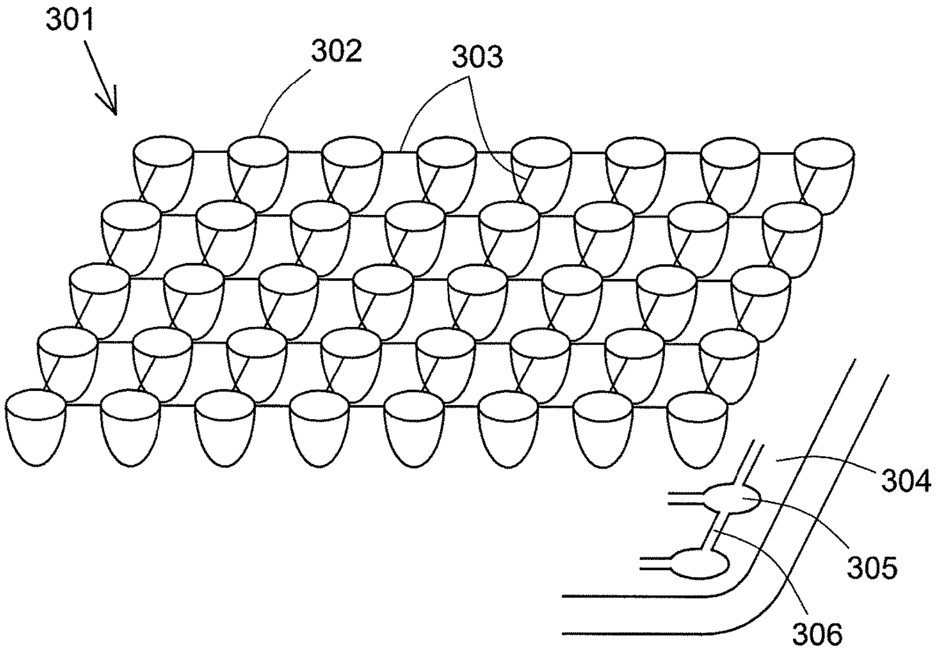
FIG. 9 is a perspective view of a sample plate designed for enhanced thermal insulation between individual wells.

One sample plate configuration is shown in FIG. 9, where the plate 301 consists of wells are formed as individual receptacles or crucibles 302 connected only by thin connecting strips or filaments 303. The filaments provide structural integrity and uniform spacing to the plate but are sufficiently thin to minimize the heat transfer between the crucibles. The filaments can be made of plastic or other material that is of relatively low thermal conductivity to further reduce crucible-to-crucible heat transfer. The crucibles 302 and filaments 303 rest on a heat transfer block 304 that has indentations 305 to receive the crucibles 302 and grooves 306 to receive the filaments 303. Individual heat transfer blocks 304 can be used for individual crucibles or groups of crucibles. The external contour of each crucible 302 is in full surface contact with the surface of an indentation 305 in the heat transfer block 304. The crucibles can have the same dimensions as the standard wells of a conventionally-used sample plate. The sample plate 301 can be molded in two shots or molding steps. In the first shot, each crucible 302 is molded of highly thermally conductive plastic. In the second shot, the filaments 303 are molded using plastic, ceramic, or other materials that are poor thermal conductors.

Figure 10:
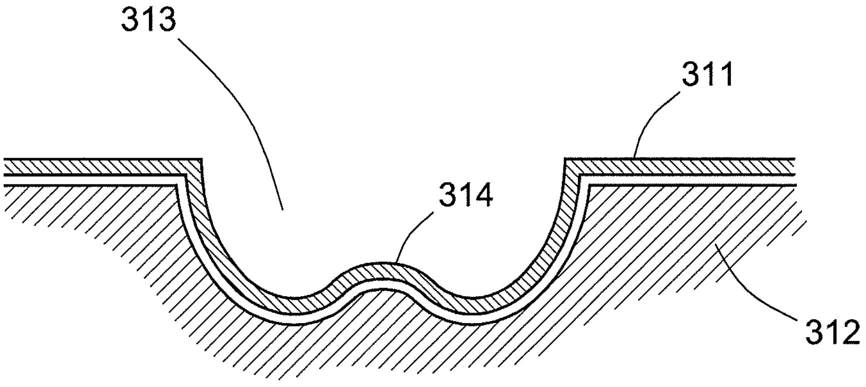
FIG. 10 is a cross section of one well of a sample plate with a structure that provides enhanced thermal contact with heating or cooling elements.

The wells or crucibles themselves can be shaped to improve the thermal contact between individual wells and a heating or cooling block positioned below the plate. An example of a sample plate with specially shaped crucibles is shown in FIG. 10, where the sample plate 311 has a contour complementary in shape to an indentation in a heat transfer block 312. One well 313 of the sample plate is shown in cross section, indicating a complex contour that is serpentine in shape, including a protrusion or bump 314 at the center of the base. This provides an increased contact surface area between the underlying heat transfer block and the walls of the well, and hence the well contents. The greater surface area is achieved without increasing the lateral dimensions of the well. Other profiles of complex contours such as more protrusions will provide the same effect. Examples are profiles that contain cross-hatching, indentations, posts, or other features that increase the surface area and improve contact between the block and the plate. The profile shown in FIG. 10 and other high-surface-area profiles can also be used in continuous sample plates of more conventional construction, where continuous webs replace the filaments 303 of FIG. 9.

Figure 11:
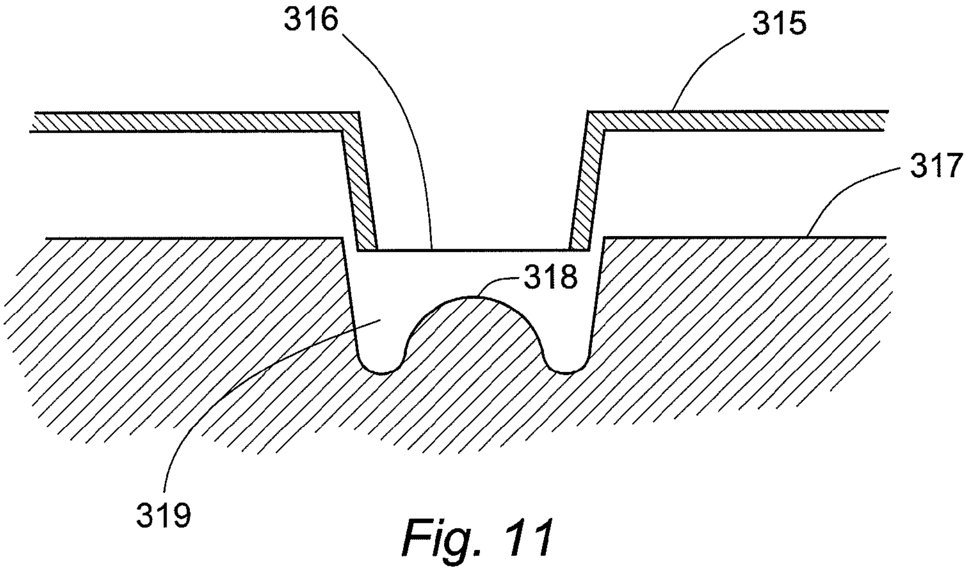
FIG. 11 is a cross section of an alternative design of a sample plate that provides enhanced thermal contact with temperature control components.

FIG. 11 depicts a variation of the plate and block combination of FIG. 11 in which the plate 315 is rigid except for the floor of each well. Forming the floor of each well is an elastic film 316 spanning the width of the well. The heat transfer block 317 is also different, with a protrusion 318 extending upward from the base of each indentation 319. The side walls of the indentations are still complementary in shape to the side walls of the wells, and the elastic base 316 of each well will stretch around the protrusion 318 in each well to provide full surface contact between the entire base and walls of each well in the sample plate and the inner surface of each indentation in the block. An advantage of this design is that when the plate 315 is removed from the block 317, the liquids occupying the well are readily aspirated.

The sample plates described above can be manufactured from any conventional material used in analytical or laboratory devices or sample handling equipment, as well as materials that offer special or enhanced properties that are especially effective in heat transfer. One such group of materials are thermally conducting plastics or non-plastic materials with high thermal conductivity. Thermal conductivity can also be improved by electroplating. The plate material can be selected for its magnetic properties, ultrasonic-interaction properties, RF-interaction properties, or magnetostrictive properties. The plates can be formed by a variety of manufacturing methods, including blast methods, thermal forming, and injection molding. As an alternative, the sample plate can be dispensed with entirely, and samples can be placed directly in indentations in the surface of a coated block.

Figure 12A:
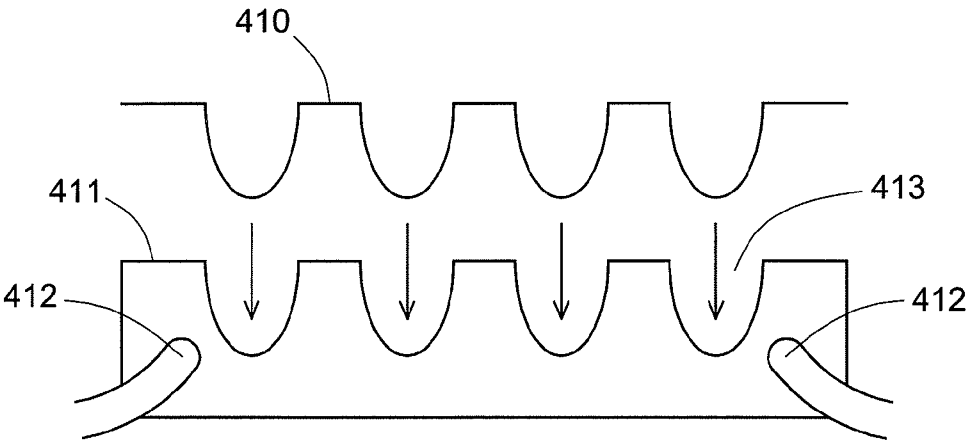
FIGS. 12*a* through 12*c* are cross sections of still further constructions that provide enhanced thermal contact between a sample plate and heating or cooling elements.
Figure 12B:
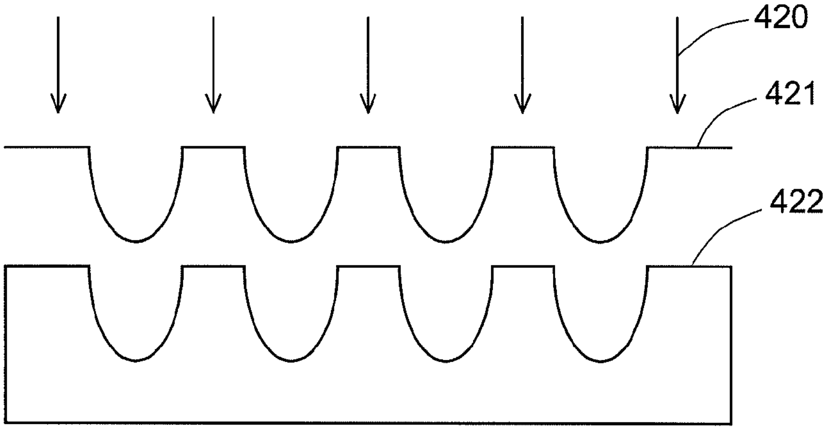

Thermal contact between the sample plate and heating or cooling blocks can be further optimized or improved by a variety of methods. FIG. 12*a* illustrates one such method in which the plate 410 and the block 411 are complementary in shape, and the plate is forced against the block by a partial vacuum drawn through ports 412 in the block. Although not shown, the indentations 413 in the block contain small openings that transmit the vacuum to the underside of the plate 410. An alternative is to apply pressure to the plate from above, as illustrated in FIG. 12*b*, where pneumatic pressure 420 above the plate 421 forces the plate against the block 422. Alternatives to pneumatic pressure are pressure applied by mechanical means and by fluidic means.

Figure 12C:
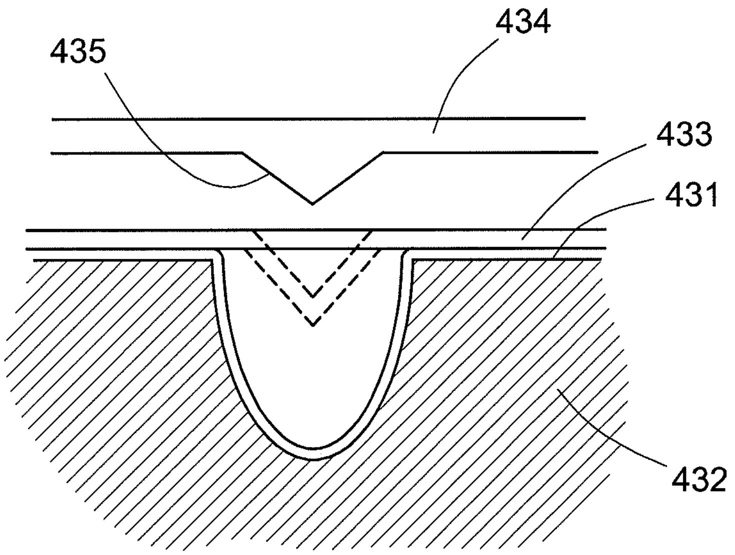

A third construction for pressing the wells of the plate against the temperature block is shown in FIG. 12*c*. In this construction, the plate 431 and block 432 are again complementary in shape, but a flexible, and preferably elastic, sealing film 433 is placed over the top of each well. An optically clear pressure block 434 is placed over the sealing film. On the underside of the pressure block 434 are protrusions 435 that press against the sealing film 433 and cause the sealing film to expand and bulge into the interior of each well, as indicated by the dashed lines, thereby applying pressure to the contents of each well which in turn forces the walls of the well against the block. The optically transparent character of the pressure block 434 allows illumination of the well contents and signal detection, both from above the sample plate. A transparent lid heating element (i.e., a glass of plastic block with a resistance coating) can be used in place of the pressure block, and a pad can be inserted between the lid heating element and the plate assembly to transmit pressure from the lid to the plate assembly. The pad can be of opaque material with an opening above each well to permit optical measurement from above. Alternatively, the pad can contain a series of small holes similar to a screen to allow imaging, while providing a surface to transfer pressure to the film.

Detection of the temperatures in the individual reaction zones and thermal domains can be performed in conjunction with the various methods of temperature control. Individual temperature sensors such as thermistors or thermocouples, for example, can be used. Temperatures can also be detected by measurements of the resistivities of the solutions in individual wells by incorporating one or more holes plated with conductive material in each well and measuring the resistance between contacts on the backs of the wells. Temperatures can also be detected by measuring the resistivity of the block itself or of the sample plate. This can be done with a rectangular array of wells by passing either DC or AC currents through the array in alternating directions that are transverse to each other and taking alternating measurements of the current. The resulting data is processed by conventional mathematical relations (two equations with two unknowns each) to provide a multiplexed resistance measurement for all points in the block. This procedure can also be used on the plate itself, particularly by coating the plate with a resistive material that offers a greater change of resistance with temperature. The plate can also be constructed from materials that have particular resistance properties achieved for example by metals, carbon, or other materials embedded in the plate. A further method is by the use of a non-contact two-dimensional infrared camera to provide relative temperatures which can be quantified by a separate calibration temperature probe. Still further methods include detecting color changes or variations in the plate as an indication of temperature, or color changes or variations in the samples. Color changes can be detected by a real-time camera. As a still further alternative, a sensor with a transponder can be embedded in the plate. A still further alternative is one that seals the well contents at a fixed volume and measures the pressure inside the well as an indication of temperature, using the ideal gas relation $pV=nRT$. Magnetic field changes can also be used, by using blocks of appropriate materials that produce a magnetic field that varies with temperature. A still further alternative is an infrared point sensor. In addition, sensors can be incorporated into the Peltier devices. Also, embedded bimetallic strips can be used as well as individual sensors inside thermal probes.

Figure 13:
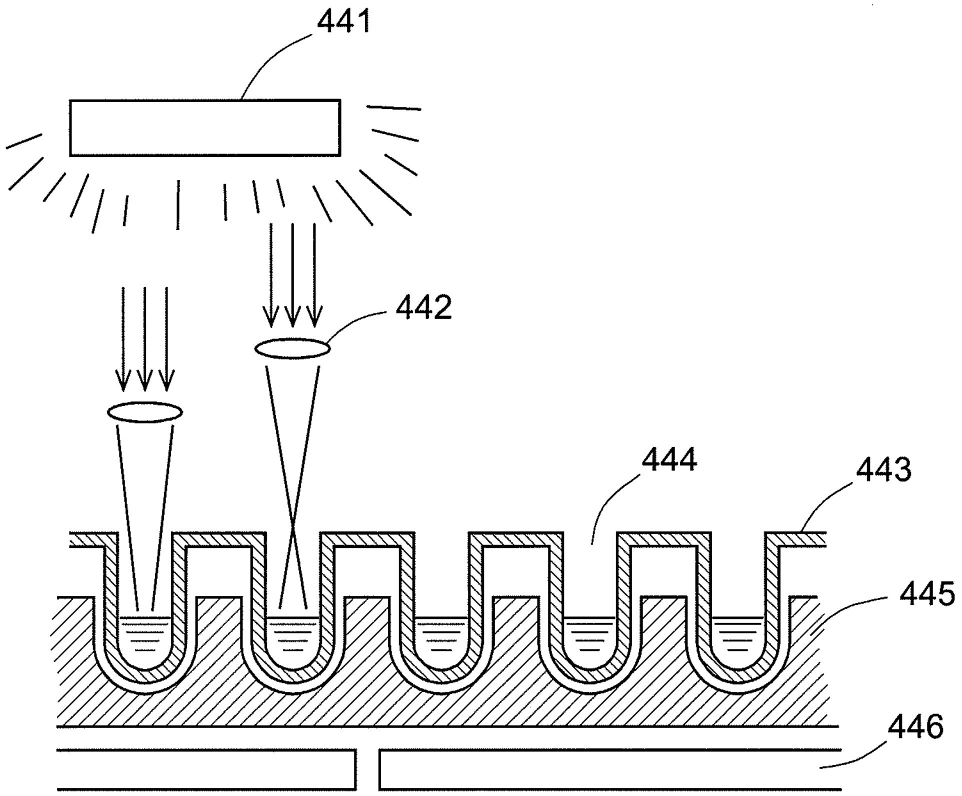
FIG. 13 is a cross section of a further method of providing localized heating for use in conjunction with the localized temperature control systems of the preceding figures.

While various heating methods and elements have been discussed above for use in conjunction with Peltier devices that are arranged for cooling, one of these methods is heating by light energy. FIG. 13 depicts a construction in which localized heating of individual wells is achieved by radiation from a light source 441. Light from the light source is concentrated through a series of focusing lenses 442 that are aimed at the sample plate 443, using a separate lens for each well 444 of the plate and either a common light source 441 as shown or a separate light source for each well. By moving any single lens 442 up and down, the light rays are brought into and out of focus to vary the amount of heat transferred to the sample. The temperature of each well can thus be modulated individually. The block 445 underneath the sample plate provides either heat transfer to underlying Peltier devices 446. Localized heating in this manner can be applied to any number of wells or thermal domains.

What is claimed is:

1. Apparatus for performing polymerase chain reactions in a plurality of samples, said apparatus comprising:

a plurality of thermally conductive sample blocks for polymerase chain reactions, arranged in a fixed horizontal array, wherein each sample block comprises a plurality of sample wells and is configured to retain a plurality of samples;

a plurality of independently controlled thermoelectric modules, a thermoelectric module positioned underneath each said sample block, wherein the thermoelectric modules are configured to cycle the temperatures of the sample blocks for polymerase chain reactions;

a layer of thermally conductive material between each sample block and each thermoelectric module; and a solid barrier of thermally insulating material positioned between each pair of adjacent sample blocks to thermally isolate the sample blocks of the pair from each other.

2. The apparatus of claim 1, wherein the thermally conductive material is selected from the group consisting of an adhesive, grease, putty, and paste.

3. The apparatus of claim 1 further comprising heat sink means thermally coupled to said plurality of thermoelectric modules to dissipate heat generated by said thermoelectric modules.

4. The apparatus of claim 3 wherein said heat sink means is a single heat sink common to all thermoelectric modules.

5. The apparatus of claim 3 wherein said heat sink means comprises an individual heat sink for each thermoelectric module.

6. The apparatus of claim 1 wherein said fixed horizontal array is a two-dimensional array.

7. The apparatus of claim 1 wherein the plurality of sample wells of each sample block is configured to receive a sample plate or portion thereof.

8. The apparatus of claim 1 wherein two or more thermoelectric modules are positioned underneath each said sample block.

9. A method for independently controlling temperatures of polymerase chain reactions in a plurality of samples retained in a plurality of thermally conductive sample blocks of the apparatus of claim 1, said method comprising:

supplying electric power to thermoelectric modules of the apparatus while controlling the magnitude of power supplied to each of said thermoelectric modules independently, thereby maintaining or changing the temperature of each sample block independently of other sample blocks.

10. The method of claim 9, wherein the thermally conductive material is selected from the group consisting of an adhesive, grease, putty, and paste.

11. The method of claim 9, further comprising drawing heat from said thermoelectric modules by heat sink means.

12. The method of claim 11, wherein said heat sink means is a single heat sink common to all thermoelectric modules.

13. The method of claim 11, wherein said heat sink means comprises an individual heat sink for each thermoelectric module.

14. The method of claim 9, wherein said sample blocks are arranged in a fixed horizontal two-dimensional array.

15. The method of claim 9, wherein the plurality of sample wells of each sample block is configured to receive a sample plate or portion thereof.

16. The method of claim 9, wherein two or more thermoelectric modules are positioned underneath each said sample block.

* * * * *